United States Patent [19]

Galliani et al.

[11] Patent Number: 4,948,804
[45] Date of Patent: Aug. 14, 1990

[54] DERIVATIVES OF 1-BENZOYL 2-OXO 5-ALKOXY PYRROLIDINE, THEIR PREPARATION, THEIR USE AS MEDICAMENTS AND THE COMPOSITIONS CONTAINING THEM

[75] Inventors: Giulio Galliani; Fernando Barzaghi, both of Monza; Carlo Zirotti, Arona; Emilio Toja, Milan, all of Italy

[73] Assignee: Roussel Uclaf, Paris, France

[21] Appl. No.: 211,287

[22] Filed: Jun. 24, 1988

[30] Foreign Application Priority Data

Jun. 26, 1987 [IT] Italy ............... 21079 A/87

[51] Int. Cl.⁵ .................... A61K 31/40; C07D 207/12
[52] U.S. Cl. ..................................... 514/423; 548/539
[58] Field of Search .................... 548/539; 514/423

[56] References Cited

U.S. PATENT DOCUMENTS

| | | | |
|---|---|---|---|
| 2,915,430 | 12/1959 | Taber | 514/423 |
| 3,117,975 | 1/1964 | Bortnick et al. | 548/545 |
| 3,423,426 | 1/1969 | Kohn | 548/542 |
| 3,686,169 | 8/1972 | Coran et al. | 548/542 |
| 4,118,500 | 10/1978 | Mitzlaff et al. | 514/423 X |
| 4,239,770 | 12/1980 | Kyburz et al. | 514/423 X |
| 4,369,139 | 1/1983 | Kyburz et al. | 548/539 |
| 4,452,807 | 6/1984 | Aschwanden et al. | 514/423 |
| 4,585,769 | 4/1986 | Roger et al. | 514/423 X |
| 4,772,601 | 9/1988 | Martin | 514/423 X |

FOREIGN PATENT DOCUMENTS

0138721 4/1985 European Pat. Off. .
2055835 3/1981 United Kingdom ............... 514/423

OTHER PUBLICATIONS

Noller, "Chemistry of Organic Compounds", (1965), 3rd Ed., p. 268; W. B. Saunders, Co., Philadelphia and London.
Drugs of the Future, vol. 10, No. 12, [1985], pp. 972, 974.

Primary Examiner—Joseph Paul Brust
Attorney, Agent, or Firm—Stevens, Davis, Miller & Mosher

[57] ABSTRACT

Compounds useful in the treatment of patients suffering from intellectual or nervous asthenias, memory failures, senescence or mental strain of the formula (I):

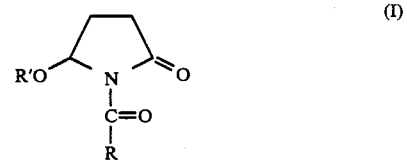

in which R' represents hydrogen, linear, branched or cyclic alkyl containing up to 12 carbon atoms, alkenyl containing from 2 to 8 carbon atoms, acyl containing from 1 to 6 carbon atoms or aralkyl containing from 7 to 15 carbon atoms and R represents aryl containing up to 14 carbon atoms, optionally substituted, or a mono- or polycryclic heterocyclic aromatic radical, optionally substituted; also therapeutic compositions containing those compounds and method of use.

22 Claims, No Drawings

DERIVATIVES OF 1-BENZOYL 2-OXO 5-ALKOXY PYRROLIDINE, THEIR PREPARATION, THEIR USE AS MEDICAMENTS AND THE COMPOSITIONS CONTAINING THEM

This invention relates to new derivatives of 1-benzoyl 2-oxo 5-alkoxy pyrrolidine, their preparation, their use as medicaments and the compositions containing them.

A subject of the invention is compounds of formula (I):

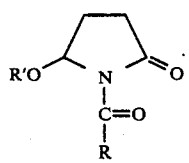

in which R' represents hydrogen, linear, branched or cyclic alkyl containing up to 12 carbon atoms, alkenyl containing from 2 to 8 carbon atoms, acyl containing from 1 to 6 carbon atoms or aralkyl containing from 7 to 15 carbon atoms and R represents aryl containing up to 14 carbon atoms, optionally substituted, or a mono- or polycyclic heterocyclic aromatic radical, optionally substituted.

As alkyl there is preferred an alkyl containing from 1 to 8 carbon atoms, for example, methyl, ethyl, n-propyl, isopropyl, n-butyl, isobutyl, tertbutyl, n-pentyl, n-hexyl, n-heptyl, n-octyl, cyclopropyl, cyclobutyl, cyclopentyl or cyclohexyl.

As alkenyl there is preferred ethenyl, propenyl or butenyl.

As acyl there is preferred acetyl, propionyl or butyryl, as noted these are alkanoyl acyl groups.

As aralkyl there is preferred phenalkyl, particularly phenalkyl of 7 to 15 carbon atoms, e.g. benzyl or phenethyl.

As aryl there is preferred phenyl or biphenylyl.

As heterocyclic radical there is preferred furyl, thienyl, pyranyl, pyridyl, benzofuranyl, isobenzofuranyl, chromanyl, isochromanyl, chromenyl, xanthenyl, phenoxathienyl, oxazolyl, isooxazolyl, furazanyl, phenoxazinyl, thieno [2,3-b] furanyl, 2H-furo [3,2-b]-pyranyl, benzoxazolyl or morpholinyl.

When the radical R is substituted, it preferably carries as substituents one or more substituents chosen from the group constituted by a free, esterified or etherified hydroxy radical in which the ester or ether part contains from 1 to 18 carbon atoms, as for example acetoxy, methoxy or benzyloxy, ketone and oxime functions, linear, branched or cyclic alkyl, saturated or unsaturated, containing up to 18 carbon atoms, for example methyl, ethyl, propyl or isopropyl, ethenyl or ethynyl, halogen atoms, such as fluorine, chlorine, and bromine, the following groups: $CF_3$, $SCF_3$, $OCF_3$, $NO_2$, $NH_2$ or $C\equiv N$, phenyl, acyl and alkoxy-carbonyl groups containing from 2 to 8 carbon atoms and alkylsulphonyl groups containing from 1 to 6 carbon atoms.

More particularly, a subject of the invention is compounds of formula (I) in which R represents optionally substituted phenyl, as well as those in which R represents a linear, branched or cyclic alkyl containing up to 12 carbon atoms as for example n-pentyl, n-hexyl, n-heptyl or n-octyl.

A subject of the invention is in particular compounds of formula (I), the preparation of which is given further on in the examples.

Among the preferred compounds of the invention, there can be cited the compounds of Examples 7 and 10.

The compounds of the invention present useful pharmacological properties: they retard the extinction of the conditioned avoidance response and they retard the disappearance of the learned response. They help attention, vigilance and memory.

A subject of the invention is therefore compounds of formula (I) as medicaments, useful in particular in the treatement of intellectual or nervous asthenias, memory failures, aging and mental fatigue.

A subject of the invention, as medicaments, is more particularly the products of Examples 7 and 10.

The usual daily dose is variable according to the affection concerned, the patient treated and the administration route; it can be between 0.6 mg and 40 mg/kg for example between 2 and 20 mg/kg in one or more doses for the product of Example 7 administered by oral route.

A subject of the present invention is also pharmaceutical compositions containing as active principle at least one compound of formula (I).

The pharmaceutical compositions of the invention can be solid or liquid and be presented in the pharmaceutical forms currently used in human medicine, for example, plain or sugar-coated tablets, capsules, granules, suppositories and injectable preparations; they are prepared according to standard methods.

The active principle can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing and emulsifying agents, and preservatives.

A subject of the invention is also a process for preparing compounds of formula (I), characterized in that a compound of formula (II):

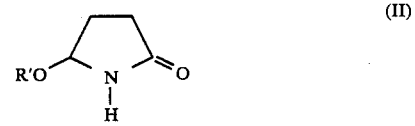

in which R' keeps the same significance as previously indicated, is submitted to the action of a compound of formula (III):

in which Hal represents chlorine or bromine and R keeps the same significance as previously indicated, in order to obtain a corresponding compound of formula (I).

In a preferred method of the invention, the reaction between the product of formula (II) and the product of formula (III) is carried out:
(a) in the presence of a strong base such as pyridine, butyllithium, an alkaline hydride such as sodium hydride or sodium bis-(trimethylsilyl)amide;
(b) in a solvent chosen from the group constituted by tetrahydrofuran, benzene, dimethylformamide, dimethylsulphoxide, dioxane or the diethyl ether of diethylene glycol.

The compounds of formula (II) used as starting compounds are products known in a general way which can be prepared according to the process described in Tetrahedron 31, 1437 (1975) or Tetrahedron 41, 2007 (1985) or according to the process described in Heterocycles 22, 1733 (1984).

The preparation of some products with the formula (I) is given further on in the examples.

The following examples illustrate the invention without however limiting it.

EXAMPLE 1

1-benzoyl 5-ethoxy pyrrolidin-2-one 12 g of benzoyl chloride is added to a solution of 11 g of 5-ethoxy pyrrolidin-2-one in 64 cm$^3$ of pyridine cooled to $-5°$ C., with agitation for 8 hours at 0° C. After 16 hours at rest, agitation is resumed for 8 hours at ambient temperature followed by dilution with 500 cm$^3$ of water and extraction with chloroform. The solvent is then evaporated and the residue is chromatographed on silica (eluent: benzene-ethyl acetate 5-2). Then the solvent is evaporated and the residue is distilled under 0.5 mm Hg. The product obtained is washed with an aqueous solution of sodium bicarbonate, extracted with chloroform, then the solvent is evaporated. 2.1 g of expected product is obtained. m.p. $=53°-55°$ C., isolated from petroleum ether. The sample for analysis was distilled at $130°-135°$ C. under 0.5 mm Hg.

Analysis: $C_{13}H_{15}NO_3$: Calculated: C % 66.68; H % 6.37; N % 6.03. Found: 66.93; 6.48; 6.00.

EXAMPLE 2

1-(4-methoxybenzoyl) 5-ethoxy pyrrolidin-2-one 2.6 g of sodium hydride (dispersed at 55–60% in oil) is added to a solution of 7 g of 5-ethoxy pyrrolidin-2-one in 150 cm$^3$ of dioxane, with agitation for 1 hour. A solution of 9.25 g of 4-methoxy benzoyl chloride in 60 cm$^3$ of dioxane is added with agitation for 4 hours. After filtering, the dioxane is evaporated under reduced pressure. The residue is chromatographed on 500 g of silica gel (eluent: acetone-n-hexane 1-2) and 6.35 g of expected product is obtained. b.p. $=210°$ C. under 0.09 mbar.

Analysis: $C_{14}H_{17}NO_4$: Calculated: C % 63.86; H % 6.51; N % 5.32. Found: 63.57; 6.44; 5.27.

EXAMPLE 3

1-benzoyl 5-n-propyloxy pyrrolidin-2-one 18.6 cm$^3$ of a 1.5M solution of n-butyllithium in hexane is added to a solution of 4 g of 5-(1-propyloxy) pyrrolidin-2-one in tetrahydrofuran at $-60°$ C., while maintaining the temperature between $-55°$ C. and $-60°$ C. After agitation for 15 minutes at $-60°$ C. a solution of 3.93 g of benzoyl chloride in 20 cm$^3$ of tetrahydrofuran is added at this temperature. After allowing the mixture to return to ambient temperature, the solvent is evaporated under reduced pressure. The residue is chromatographed on silica (eluent: ethyl acetate-n-hexane 1-3) and 4 g of the expected product is obtained. b.p. $=200°$ C. under 0.1 mbar.

Analysis: $C_{14}H_{17}NO_3$: Calculated: C % 68.00; H % 6.93; N % 5.66. Found: 67.77; 6.82; 5.74.

EXAMPLE 4

1-benzoyl 5-isopropyloxy pyrrolidin-2-one 11.7 cm$^3$ of a 1.6M solution of n-butyllithium in hexane is added at $-70°$ C. to a solution of 2.5 g of 5-isopropyloxy pyrrolidin-2-one in 60 cm$^3$ of tetrahydrofuran, while maintaining the temperature between $-70°$ C. and $-65°$ C. Agitation is carried out for 30 minutes under these conditions then a solution of 2.46 g of benzoyl chloride in 8 cm$^3$ of tetrahydrofuran is added, maintaining the temperature between $-65°$ C. and $-70°$ C. The temperature is allowed to return to the ambient over 2 hours. After evaporation to dryness and then chromatography on silica (eluent: ethyl acetate-n-hexane 1-3), 2.78 g of the product sought is obtained.

Analysis: $C_{14}H_{17}NO_3$: Calculated: C % 68.00; H % 6.93; N % 5.66. Found: 68.12; 7.04; 5.74.

EXAMPLE 5

1-benzoyl 5-propyloxy pyrrolidin-2-one 17 cm$^3$ of a 1.5M solution of n-butyllithium in n-hexane is added at $-60°$ C. to a solution of 4 g of 5-(1-butyloxy) pyrrolidin-2-one in 90 cm$^3$ of tetrahydrofuran. The whole is agitated for 15 minutes at $-60°$ C. then, at this temperature, a solution of 3.58 g of benzoyl chloride in 25 cm$^3$ of tetrahydrofuran is added. After allowing the temperature to return to the ambient, the solvent is evaporated under reduced pressure and the residue is chromatographed on silica (eluent: ethyl acetate-n-hexane 1-3) and 4 g of expected product is obtained. b.p. $=200°-210°$ C. under 0.07 mbar.

Analysis: $C_{15}H_{19}NO_3$: Calculated: C % 68.94; H % 7.33; N % 5.36. Found: 68.86; 7.40; 5.54.

EXAMPLE 6

1-(4-methoxybenzoyl) 5-n-propyloxy pyrrolidin-2-one 11.2 cm$^3$ of a 1.6M solution of n-butyllithium in n-hexane is added at $-40°$ C. to a solution, cooled to $-45°$ C., of 2.8 g of 5-n-butyloxy pyrrolidin-2-one in 70 cm$^3$ of tetrahydrofuran with agitation for 30 minutes. Under the same conditions, a solution of 5.24 g of anisoyl chloride (at 58% in toluene) in 6 cm$^3$ of tetrahydrofuran is added. After agitation for 2 hours, allowing to return to ambient temperature, the mixture is evaporated to dryness. The oil obtained is chromato-graphed on silica (eluent: toluene-ethyl acetate 8-2) and 2 g of the product sought is obtained.

Analysis: $C_{16}H_{21}NO_4$: Calculated: C % 65.96; H % 7.26; N % 4.81. Found: 65.39; 7.36; 5.03.

EXAMPLE 7

1-benzoyl 5-n-pentyloxy pyrrolidin-2-one 15.56 cm$^3$ of a 1.5M solution of n-butyllithium in hexane is added at $-60°$ C. to a solution of 4 g of 5-(1-pentyloxy) pyrrolidin-2-one in 80 cm$^3$ of tetrahydrofuran. Agitation is carried out for 15 minutes at $-60°$ C. and then under these conditions a solution of 3.28 g of benzoyl chloride in 20 cm$^3$ of tetrahydrofuran is added. After allowing the temperature to return to ambient, the solvent is evaporated under reduced pressure. The residue is chromatographed on silica (eluent: ethyl acetate-n-hexane 1-3) and 4 g of sought product is obtained.

Analysis: $C_{16}H_{21}NO_3$: Calculated: C % 69.79; H % 7.69; N % 5.09. Found: 69.62; 7.78; 5.19.

EXAMPLE 8

1-(4-methoxybenzoyl) 5-n-pentyloxy pyrrolidin-2-one 15.57 cm³ of a 1.5M solution of n-butyllithium in n-hexane is added at −70° C. to a solution of 4 g of 5-(1-pentyloxy) pyrrolidin-2-one in 80 cm³ of tetrahydrofuran. Agitation is carried out for 15 minutes at −70° C. then while maintaining this temperature, a solution of 3.98 g of para-anisoyl chloride at 58% in toluene is added. After allowing to return to ambient tempera-ture and evaporating under reduced pressure, the residue is chromatographed on silica (eluent: n-hexane-ethyl acetate 2-1). 5.1 g of sought product is obtained.

Analysis: $C_{17}H_{23}NO_4$: Calculated: C % 66.86; H % 7.59; N % 4.59. Found: 67.02; 7.68; 4.76.

EXAMPLE 9

1-benzoyl 5-n-hexyloxy pyrrolidin-2-one 16 cm³ of a 1.6M solution of butyllithium in hexane is added at −70° C. to 4.5 g of 5-n-hexyloxy pyrrolidin-2-one in solution in 130 cm³ of anhydrous tetrahydrofuran. Agitation is carried out for 20 minutes at −70° C. and under the same conditions a solution of 3.4 g of benzoyl chloride in 20 cm³ of tetrahydrofuran is added. After allowing to return to ambient temperature and concentration under reduced pressure, the residue is chromatographed on silica (eluent: toluene-ethyl acetate 8-2). 3.3 g of the product sought is obtained.

Analysis: $C_{17}H_{23}NO_3$: Calculated: C % 70.56; H % 8.01; N % 4.89. Found: 70.26; 7.84; 4.88.

EXAMPLE 10

1-benzoyl 5-n-heptyloxy pyrrolidin-2-one 16.5 cm³ of a 15% solution butyllithium in hexane is added at −60° C. to 4.98 g of 5-n-heptyloxy pyrrolidin-2-one in solution in 100 cm³ of tetrahydrofuran. After 20 minutes of agitation at −60° C., 3.5 g of benzoyl chloride in 25 cm³ of tetra-hydrofuran is added at this temperature. Agitation is carried out for 4 hours, allowing the mixture to return to ambient temperature. After concentration at 40° C., the residue is taken up in water, extracted with ether and concentrated to dryness. The residue is chromatographed on silica (eluent: toluene-ethyl acetate 8-2) and 1.2 g of the product sought is obtained.

Analysis: $C_{18}H_{25}NO_3$: Calculated: C % 71.26; H % 8.31; N % 4.62. Found: 71.54; 8.25; 4.53.

EXAMPLE 11

1-benzoyl 5-n-octyloxy pyrrolidin-2-one 16.5 cm³ of a 15% solution of butyllithium in hexane is added at −60° C. to 5.3 g of 5-n-octyloxy pyrrolidin-2-one in solution in 200 cm³ of tetrahydrofuran. After agitation for 20 minutes at −60° C., then, while maintaining these conditions, a solution of 3.5 g of benzoyl chloride in 50 cm³ of tetrahydrofuran is added. Agitation is continued while allowing to return to ambient temperature. After concentration and chromatography on silica (eluent: toluene-ethyl acetate 8-2), 4.2 g of the product sought is obtained.

Analysis: $C_{19}H_{27}NO_3$: Calculated: C % 71.89; H % 8.57; N % 4.41. Found: 71.69; 8.48; 4.32.

EXAMPLE 12

1-benzoyl 5-methoxy pyrrolidin-2-one 20.8 cm³ of a 1.5M solution of butyllithium in hexane is added at −70° C. to a solution of 3.8 g of 5-methoxy pyrrolidin-2-one in 160 cm³ of tetrahydrofuran. This temperature is maintained for 20 minutes, then 4.69 g of benzoyl chloride in solution in tetrahydrofuran is added. After allowing to return to ambient temperature, the mixture is concentrated to dryness and chromatographed on silica (eluent: hexane-ethyl acetate 1-1). 3 g of expected product is obtained. m.p. =92°-94° C. crystallized from isopropyl ether.

Analysis: $C_{12}H_{13}NO_3$: Calculated: C % 65.74; H % 5.98; N % 6.39. Found: 65.92; 5.96; 6.32.

EXAMPLE 13

1-(3-trifluoromethyl) benzoyl 5-n-pentyloxy pyrrolidin-2-one 17.5 cm³ of a 1.5M solution of butyllithium in hexane is added at −70° C. to a solution of 4.5 g of 5-n-pentyloxy pyrrolidin-2-one in 160 cm³ of tetrahydrofuran. This temperature is maintained for 20 minutes, then 5.48 g of 3-trifluoromethyl benzoyl chloride in solution in 20 cm³ of tetrahydrofuran is added. After allowing to return to ambient temperature, the mixture is concentrated to dryness and chromatographed on silica (eluent: hexane-ethyl acetate 75-25). 6.1 g of expected product is obtained.

Analysis: $C_{17}H_{20}F_3NO_3$: Calculated: C % 59.47; H % 5.87; N % 4.08. Found: 59.39; 5.81; 4.17.

EXAMPLE 14

1-(4-nitro) benzoyl 5-n-pentyloxy pyrrolidin-2-one 15.5 cm³ of a 1.5M solution of butyllithium in hexane is added at −70° C. to 4 g of 5-pentyloxy pyrrolidin-2-one in solution in 150 cm³ of tetrahydrofuran. The temperature is maintained at this value for 20 minutes, then a solution of 4.33 g of nitrobenzoyl chloride in 20 cm³ of tetrahydrofuran is added. The mixture is allowed to return to ambient temperature, concentrated, chromatographed on silica (eluent: hexane-ethyl acetate 8-2) and, after crystallization in isopropanol, 3.9 g of product is obtained. m.p. =56°-58° C.

Analysis: $C_{16}H_{20}N_2O_5$: Calculated: C % 59.99; H % 6.29; N % 8.74. Found: 60.17; 6.16; 8.67.

EXAMPLE 15

1-(4-diphenyl) carbonyl 5-n-pentyloxy pyrrolidin-2-one 15.3 cm³ of a 1.5M solution of butyllithium in hexane is added at −70° C. to a mixture of 3.95 g of 5-n-pentyloxy pyrrolidin-2-one in 150 cm³ of tetrahydrofuran, and the whole is maintained at this temperature for 20 minutes, then a solution of 4-diphenyl carbonyl chloride in 20 cm³ of tetrahydrofuran is added. The mixture is allowed to return to ambient temperature, concentrated to dryness and chromatographed on silica (eluent: hexane-ethyl acetate 8-2). After crystallization in isopropanol, 4.9 g of expected product is obtained. m.p. =102°-104° C.

Analysis: $C_{22}H_{25}NO_3$: Calculated: C % 75.18; H % 7.17; N % 3.99. Found: 75.02; 7.15; 4.14.

EXAMPLE 16

1-(4-fluoro) benzoyl 5-n-pentyloxy pyrrolidin-2-one 8.95 cm³ of a 1.5M solution of butyllithium in hexane is added at −70° C. to a solution of 2.3 g of 5-n-pentyloxy pyrrolidin-2-one in 110 cm³ of tetrahydrofuran. The mixture is maintained at this temperature for 20 minutes, then a solution of 2.1 g of 4-fluorobenzoyl chloride in 10 cm³ of tetrahydrofuran is added. The whole is returned to ambient temperature, concentrated to dryness and chromatographed on silica (eluent: hexane-ethyl acetate 7-3). 1.6 g of expected product is obtained.

Analysis: $C_{16}H_{20}FNO_3$: Calculated: C % 65.51; H % 6.87; N % 4.77. Found: 65.87; 6.91; 4.69.

EXAMPLE 17

1-(4-chloro) benzoyl 5-n-pentyloxy pyrrolidin-2-one 8.4 cm³ of a 1.6M solution of butyllithium in hexane is added at −70° C. to a solution of 2.3 g of 5-n-pentyloxy pyrrolidin-2-one in 130 cm³ of tetrahydrofuran. The mixture is maintained at this temperature for 20 minutes, then a solution of 2.35 g of 4-chlorobenzoyl chloride in 10 cm³ of tetrahydrofuran is added, followed by returning to ambient temperature, concentrating to dryness and chromatographing on silica (eluent: hexane-ethyl acetate 7-3). 1.9 g of expected product is obtained.

Analysis: $C_{16}H_{20}ClNO_3$: Calculated: C % 62.03; H % 6.51; N % 4.52. Found: 62.34; 6.66; 4.68.

EXAMPLE 18

1-benzoyl 5-(3-methylbutoxy) pyrrolidin-2-one 12.8 cm³ of a 1.5M solution of butyllithium in hexane is added at −70° C. to a solution of 3.3 g of 5-(3-methylbutoxy) pyrrolidin-2-one in 140 cm³ of tetrahydrofuran. The mixture is maintained for 20 minutes at this temperature, then a solution of 2.7 g of benzoyl chloride in 20 cm³ of tetrahydrofuran is added. The solution is returned to ambient temperature, concentrated to dryness under reduced pressure and chromatographed on silica (eluent: hexane-ethyl acetate 7-3) 3.5 g of expected product is obtained.

Analysis: $C_{16}H_{21}NO_3$: Calculated: C % 69.79; H % 7.69; N % 5.09. Found: 69.78; 7.69; 5.08.

EXAMPLE 19

1-benzoyl 5-(2-pentyloxy) pyrrolidin-2-one 12.4 cm³ of a 1.5M solution of butyllithium in hexane is added at −70° C. to a solution of 3.2 g of 5-(2-pentyloxy) pyrrolidin-2-one in 130 cm³ of tetrahydrofuran. The mixture is maintained at this temperature for 20 minutes, then a solution of 2.62 g of benzoyl chloride in 20 cm³ of tetrahydrofuran is added. The solution is returned to ambient temperature, concentrated and chromatographed on silica (eluent: hexane-ethyl acetate 7-3). 3.35 g of expected product is obtained.

Analysis: $C_{16}H_{21}NO_3$: Calculated: C % 69.79; H % 7.69; N % 5.09. Found: 69.91; 7.62; 5.07.

EXAMPLE 20

1-benzoyl 5-neopentyloxy pyrrolidin-2-one 2.2 g of 5-neopentyloxy pyrrolidin-2-one in 30 cm³ of ethyl ether is added at ambient temperature to a solution of 2.6 g of sodium bis trimethylsilylamide in 160 cm³ of ethyl ether. After 30 minutes, the solution is cooled to 0° C. and 1.89 g of benzoyl chloride diluted with 20 cm³ of ethyl ether is added. After leaving the solution for 30 minutes at 0° C. then allowing to return to ambient temperature, and concentrating to dryness under reduced pressure, the residue is chromatographed on silica (eluent: hexane-ethyl acetate 7-3). After crystallization from ethanol, 1.45 g of expected product is obtained. m.p.=83°-85° C.

Analysis: $C_{16}H_{21}NO_3$: Calculated: C % 69.79; H % 7.69; N % 5.09. Found: 69.63; 7.55; 5.13.

EXAMPLE 21

1-benzoyl 5-cyclopentyloxy pyrrolidin-2-one 11.8 cm³ of a 1.5M solution of butyllithium in hexane is added at −70° C. to a solution of 3 g of 5-cyclopentyloxy pyrrolidin-2-one in 140 cm³ of tetrahydrofuran. The mixture is maintained at this temperature for 20 minutes, then a solution of 2.49 g of benzoyl chloride in 20 cm³ of tetrahydrofuran is added. The whole is heated gently, then brought to dryness under reduced pressure. After chromatography on silica (eluent: hexane-ethyl acetate 7-3), 3.4 g of expected product is obtained.

Analysis: $C_{16}H_{19}NO_3$: Calculated: C % 70.31; H % 7.01; N % 5.12. Found: 70.06; 6.93; 5.15.

EXAMPLE 22

1-(4-nitro)-benzoyl-5-ethoxy-pyrrolidin-2-one 12.9 cm³ of a 1.5M solution of butyllithium in hexane is added at −70° C. to a solution of 2.5 g of 5-ethoxy-pyrrolidin-2-one in 110 cm³ of tetrahydrofuran. After 20 minutes, there is added at the same temperature 3.6 g of 4-nitrobenzoyl chloride in solution in tetrahydrofuran; the whole is returned to ambient temperature, then concentrated to dryness under reduced pressure. After crystallization from ethanol, 2.5 g of the expected product is obtained, m.p. 102°-104° C.

Analysis: $C_{13}H_{14}N_2O_5$: Calculated: C % 56.11; H % 5.07; N % 10.07. Found: 56.15; 5.01; 9.96.

EXAMPLE 23

1-(4-diphenyl)-carbonyl-5-ethoxy-pyrrolidin-2-one 7.7 cm³ of a 1.5M solution of butyllithium in hexane is added at −70° C. to a solution of 1.5 g of 5-ethoxy-pyrrolidin-2-one in 75 cm³ of tetrahydrofuran. After 20 minutes, there is added at this temperature 2.5 g of 4-diphenylcarbonyl chloride in solution in 15 cm³ of tetrahydrofuran; the whole is returned to ambient temperature, then concentrated to dryness under reduced pressure. The residue is chromatographed on silica, (eluent: hexane-ethyl acetate, 7-3) and 2.1 g of the expected product is obtained, m.p. 91°-93° C. after crystallizing from ethanol.

Analysis: $C_{19}H_{19}NO_3$: Calculated: C % 73.77; H % 6.19; N % 4.53. Found: 73.56; 6.13; 4.45.

EXAMPLE 24

1-(3-trifluoromethyl)-benzoyl-5-ethoxy-pyrrolidin-2-one 12.9 cm³ of a 1.5M solution of butyllithium in hexane is added at −70° C. to a solution of 2.5 g of 5-ethoxy-pyrrolidin-2-one in 110 cm³ of tetrahydrofuran. After 20 minutes at this temperature, there is added a solution of 4.04 g of 3-trifluoromethyl benzoyl chloride in tetrahydrofuran. After re-heating to ambient temperature, concentrating and chromatographing on silica, (eluent: hexane-ethyl acetate, 7-3), 3.4 g of the expected product is obtained.

Analysis: $C_{14}H_{14}FNO_3$: Calculated: C % 55.82; H % 4.68; N % 4.65. Found: 55.06; 4.73; 4.81.

EXAMPLE 25

1-(4-nitro)-benzoyl-5-n-butoxy-pyrrolidin-2-one 10.2 cm³ of a 1.5M solution of butyllithium in hexane is added at −70° C. to a solution of 2.4 g of 5-n-butyloxy-pyrrolidin-2-one in 100 cm³ of tetrahydrofuran. After 20 minutes at this temperature, there is added a solution of 4-nitrobenzoyl chloride in 15 cm³ of tetrahydrofuran. After returning to ambient temperature, concentrating, taking up with water and filtering, there is obtained, after crystallizing from ethanol, 2 g of the expected product. m.p. 56°–59° C.

Analysis: $C_{15}H_{18}N_2O_5$: Calculated: C % 58.82; H % 5.92; N % 9.15. Found: 59.01; 5.96; 8.97.

EXAMPLE 26

1-(4-diphenyl)carbonyl-5-n-butoxy-pyrrolidin-2-one 7.7 cm³ of a 1.5M solution of butyllithium in hexane is added at −70° C. to a solution of 1.8 g of 5-n-butyloxy-pyrrolidin-2-one in 85 cm³ of tetrahydrofuran. After 20 minutes at this temperature, there is added a solution of 2.5 g of 4-diphenylcarbonyl chloride in tetrahydrofuran. This is concentrated to dryness after allowing the temperature to return to ambient, then chromatographed on silica, (eluent: hexane-ethyl acetate, 7-3), and after crystallizing from isopropanol, 2.5 g of the expected product is obtained. m.p. 101°–103° C.

Analysis: $C_{21}H_{23}NO_3$: Calculated: C % 74.75; H % 6.87; N % 4.15. Found: 74.81; 6.92; 4.06.

EXAMPLE 27

1-(3-trifluoromethyl)benzoyl-5-n-butoxy-pyrrolidin-2-one 9.7 cm³ of a 1.5M solution of butyllithium in hexane is added at −70° C. to a solution of 2.3 g of 4-butoxy-pyrrolidin-2-one in 110 cm³ of tetrahydrofuran. After 20 minutes at this temperature, a solution of 3.06 g of 3-trifluoromethyl benzoyl in tetrahydrofuran is added, followed by returning to ambient temperature, concentrating to dryness and chromatographing on silica, (eluent: hexane-ethyl acetate, 7-3). 3 g of the expected product is obtained.

Analysis: $C_{16}H_{18}F_3NO_3$: Calculated: C % 58.36; H % 5.51; N % 4.25. Found: 58.69; 5.39; 4.48.

PREPARATION 1

5-isopropoxy pyrrolidin-2-one 28.4 g of succinimide in 1200 cm³ of isopropanol is cooled to −10° C., 32.8 g of hydride of boron and sodium is added, and after agitating for 4 hours at 0°/−10° C., there is added a 2N solution of hydrochloric acid in isopropanol, adjusting the pH to 2-3. This is maintained for 2 hours at 0° C., then neutralised with a solution of potassium hydroxide in isopropanol. The solvent is evaporated under reduced pressure, the residue is taken up with chloroform, concentrated to dryness under reduced pressure, and 20.5 g of the expected product is obtained. m.p. 68°–71° C.

PREPARATION 2

5-n-propyloxy pyrrolidin-2-one

The operation is done as for preparation 1, using n-propanol instead of isopropanol. 27.5 g of the expected product is obtained. m.p. = 52°–54° C.

PREPARATION 3

5-n-butyloxy-pyrrolidin-2-one

The operation is done as for preparation 1, using n-butanol. 7.5 g of the expected product is obtained, m.p. 36°–38° C.

This product can also be obtained by anodic alkoxylation of the pyrrolidin-2-one according to the process described in Synthesis 4, 315–317 (1980).

PREPARATION 4

5-n-pentyloxy-pyrrolidin-2-one

A mixture of 2.5 g of 5-hydroxy-pyrrolidin-2-one and 1.25 g of Amberlite IR 120 H is agitated at 65° C. for 3 hours in 55 cm³ of n-pentanol. After cooling to ambient temperature, filtering, and distilling under reduced pressure, the residue is chromatographed on silica (eluent: ethyl acetate), and 2.68 g of the expected product is obtained. m.p. 42°–43° C.

Analysis: $C_9H_{17}NO_2$: Calculated: C % 63.13; H % 10.01; N % 8.18. Found: 63.31; 9.95; 8.27.

PREPARATION 5

5-n-hexyloxy-pyrrolidin-2-one

A mixture of 0.4 g of 5-hydroxy-pyrrolidin-2-one, 10 cm³ of n-hexanol and 0.2 g of Amberlite IR 120 H is agitated at 60° C. for 3 hours. After cooling, the solvent is distilled off and the residue is chromatographed on silica, (eluent: ethyl acetate); 0.5 g of the product sought is obtained. m.p. 35°–37° C., crystallized from hexane.

Analysis: $C_{10}H_{19}NO_2$: Calculated: C % 64.83; H % 10.34; N % 7.56. Found: 64.67; 10.25; 7.49.

PREPARATION 6

5-n-heptyloxy-pyrrolidin-2-one

A mixture of 8 g of 5-hydroxy-pyrrolidin-2-one, 100 cm³ of n-heptanol and 4 g of Amberlite IR 120 H is agitated at 60° C. for 4 hours. After filtering and distilling to dryness, 11.9 g of the expected product is obtained, m.p. 52°–54° C., crystallized from hexane.

Analysis: $C_{11}H_{21}NO_2$: Calculated: C % 66.29; H % 10.62; N % 7.03. Found: 66.13; 10.51; 6.98.

PREPARATION 7

5-n-octyloxy-pyrrolidin-2-one

A mixture of 7.5 g of 5-hydroxy-pyrrolidin-2-one in 10 cm³ of n-octanol and 4 g of Amberlite IR 120 H is agitated at 60° C. for 4 hours. After filtering, and concentrating to dryness, 5.5 g of the expected product is obtained, m.p. 36°–38° C., crystallized from hexane. By re-crystallizing from hexane, m.p. = 38°–40° C.

Analysis: $C_{12}H_{23}NO_2$: Calculated: C % 67.56; H % 10.87; N % 6.57. Found: 67.32; 10.73; 6.69.

PREPARATION 8

5-(3-methylbutoxy)-pyrrolidin-2-one 5.5 g of 5-ethoxy-pyrrolidin-2-one, 30 cm³ of 3-methyl-butanol and 2.75 g of Amberlite-15 resin are agitated for 5 hours at ambient temperature. After leaving in the refrigerator for 18 hours, there is obtained, after filtering, 4.1 g of the expected product. m.p. 73°–75° C.

Analysis: $C_9H_{17}NO_2$: Calculated: C % 63.13; H % 10.0; N % 8.18. Found: 62.88; 10.06; 8.32.

PREPARATION 9

5-(2-pentyloxy)-pyrrolidin-2-one 5.5 g of 5-hydroxy-pyrrolidin-2-one, 30 cm³ of 2-pentanol and 2.75 g of Amberlite-15 resin are agitated for 5 hours at ambient temperature. After filtering, the excess pentanol is distilled off under 1 mm Hg at 40° C. The residue is chromatograp:hed on silica, (eluent: ethyl acetate), and 3.7 g of the expected product is obtained.

PREPARATION 10

5-neopentyloxy-pyrrolidin-2-one 35 g 2,2-dimethyl propanol (previously melted at 45° C.), 6 g of 5-ethoxy pyrrolidin-2-one and 3 g of Amberlite-15 resin are agitated at 40° C. for 2 hours 15 minutes. After filtering, the 2,2-dimethyl propanol is distilled off under 0.8 mm/Hg at 35° C. The residue is dissolved in hexane and iced for 2 hours. 3.2 g of the expected product is obtained, m.p. 67°–69° C., crystallized from hexane.

Analysis: $C_9H_{17}NO_2$: Calculated: C % 63.13; H % 10.0; N % 8.18. Found: 62.85; 9.81; 8.20.

EXAMPLES OF PHARMACEUTICAL COMPOSITIONS (a) Tablets were prepared of the following formula:
Product of example 7: 100 mg
Excipient q.s. for a tablet finished at: 300 mg
(Detail of excipient: lactose, corn starch, treated starch, rice starch, magnesium stearate, talc).

(b) Capsules were prepared of the following formula:
Product of example 10: 200 mg
Excipient q.s. for a tablet finished at: 300 mg
(Detail of excipient: talc, magnesium stearate, aerosil).

PHARMACOLOGICAL STUDY

Acute toxicity and behaviour

There were used male mice (Charles Rivers $CD_1$) weighing 22–23 g, without food for 16 hours. The products were administered to them by oral route at doses of 1000–500–250 mg/kg.

The effect of the products on the behaviour of the animals was evaluated according to the method described by Irvin (Psychopharmacologia (1968), 13, 222-257) during the first 8 hours and on the 24th hour.

The mortality was noted during the 7 days following the treatment.

The $LD_{50}$ was thus found to be greater than 1000 mg/kg on the products of examples 1 to 11.

Learning and Memorizing

There were used male mice (Charles Rivers $CD_1$) weighing 25–30 g. The animals were placed in the luminous part of a box with two compartments communicating by an opening (G. Galliani, F. Barzaghi and R. Cesana, Med. Sci. Res. 15, 313-314 (1987).

At the instant when the mouse passes from the luminous compartment to the dark compartment, the opening closes and it is immediately punished by an electric discharge to the paws. The animal submitted to this procedure learns to memorize the punishment. In fact, if it is put back in the luminous compartment, it will thus avoid crossing the opening and re-entering the dark compartment.

In order to induce a retrograde amnesia, the animals are submitted immediately after learning to an electric shock. After the electric shock, the products are administered by oral route at different doses.

We used from 20 to 50 animals per dose.

The anti-amnesic effect of the products is evaluated 3 hours after the treatment, using the same procedure as that utilized for the acquisition.

The time taken by the animal to return to the dark chamber (time limit 180 seconds) is used as evaluation parameter.

Under the same experimental conditions, the control animals enter with a time lapse of 40–50 seconds.

The active products are those which cause a significant increase in the latency time, with a bell-shaped dose-response curve.

The results are expressed as percentages of the increase of the latency time in comparison with the corresponding controls. Results obtained with two reference products are provided.

The following Table shows the results:

TABLE

| | Percentage increase in latency time in comparison with the controls | | | | |
|---|---|---|---|---|---|
| | Dose mg/kg per os | | | | |
| Product of example | 400 | 200 | 100 | 50 | 25 |
| 7 | — | 55* | 118* | 83* | 32 |
| 10 | 6 | 99* | 66* | 28 | 34 |
| PIRACETAM | — | 20 | 48* | 10 | 19 |
| AMIRACETAM | — | 32 | 88* | 77 | 39 |

*Values statistically different in comparison with controls.

CONCLUSION

The products of examples 7 and 10 are seen to be more active than the controls. They particularly improve the behaviour of the animals in a larger range of doses than in the case of Amiracetam or Piracetam.

What is claimed is:

1. Compounds of formula (I):

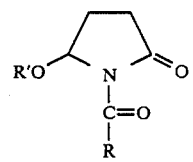

in which R' represents linear, branched or cyclic alkyl containing up to 12 carbon atoms, alkenyl containing from 2 to 8 carbon atoms, alkanoic-acyl containing from 1 to 6 carbon atoms or aralkyl containing from 7 to 15 carbon atoms and R represents aryl containing up to 14 carbon atoms, optionally substituted with a free, esterified or etherified hydroxy radical wherein said esterifying group is a carboxylic acid group containing up to 18 carbon atoms and said etherifying group is an alkyl group containing up to 18 carbon atoms, benzyloxy, alkyl up to 18 carbon atoms, cyclic alkyl up to 18 carbon atoms, unsaturated alkyl up to 18 carbon atoms, halogeno, $CF_3$, $SCF_3$, $OCF_3$, $NO_2$, $CN$, phenyl, alkanoicacyl, alkoxy carbonyl groups containing from 2 to 8 carbon atoms or alkyl sulphonyl groups containing up to 6 carbon atoms.

2. Compounds of formula (I) as defined in claim 1, in which R represents optionally substituted phenyl.

3. Compounds of formula (I) as defined in claim 1 or 2, in which R' represents a linear, branched or cyclic alkyl containing up to 12 carbon atoms.

4. Compounds as defined in claim 3, in which R' represents n-pentyl, n-hexyl, n-heptyl or n-octyl.

5. A compound of formula (I) as defined in claim 1, selected from the group consisting of 1-benzoyl 5-(n-pentyloxy) pyrrolidin 2-one and 1-benzoyl 5-(n-heptyloxy) pyrrolidin 2-one.

6. Compounds of formula (I) as defined in claim 1, in which R' represents a linear, branched or cyclic alkyl containing up to 12 carbon atoms.

7. A therapeutic composition for the treatment of patients suffering from intellectual or nervous asthenias, comprising a therapeutically effective amount of a compound as defined in any one of claims 1, 2, 4 or 5, and a pharmaceutically acceptable carrier.

8. A therapeutic composition for the treatment of patients suffering from memory failures, comprising a therapeutically effective amount of a compound as defined in any one of claims 1, 2, 4 or 5, and a pharmaceutically acceptable carrier.

9. A therapeutic composition for the treatment of patients suffering from senescence, comprising a therapeutically effective amount of a compound as defined in any one of claims 1, 2, 4 or 5, and a pharmaceutically acceptable carrier.

10. A therapeutic composition for the treatment of patients suffering from mental strain, comprising a therapeutically effective amount of a compound as defined in any one of claims 1, 2, 4 or 5, and a pharmaceutically acceptable carrier.

11. A therapeutic composition for the treatment of patients suffering from intellectual or nervous asthenias, comprising a therapeutically effective amount of a compound as defined in claim 3, and a pharmaceutically acceptable carrier.

12. A therapeutic composition for the treatment of patients suffering from memory failures, comprising a therapeutically effective amount of a compound as defined in claim 3, and a pharmaceutically acceptable carrier.

13. A therapeutic composition for the treatment of patients suffering from senescence, comprising a therapeutically effective amount of a compound as defined in claim 3, and a pharmaceutically acceptable carrier.

14. A therapeutic composition for the treatment of patients suffering from mental strain, comprising a therapeutically effective amount of a compound as defined in claim 3, and a pharmaceutically acceptable carrier.

15. A method for the treatment of patients suffering from intellectual or nervous asthenias, comprising administering to the patient an anti-intellectual asthenia or anti-nervous asthenia therapeutically effective amount of a compound as defined in claims 1, 2, 4 or 5.

16. A method for the treatment of patients suffering from memory failure, comprising administering to the patient an anti-memory failure therapeutically effective amount of a compound as defined in claims 1, 2, 4 or 5.

17. A method for the treatment of patients suffering from senescence, comprising administering to the patient an anti-senescence therapeutically effective amount of a compound as defined in claims 1, 2, 4 or 5.

18. A method for the treatment of patients suffering from mental strain, comprising administering to the patient an anti-mental strain therapeutically effective amount of a compound as defined in claims 1, 2, 4 or 5.

19. A method for the treatment of patients suffering from intellectual or nervous asthenias, comprising administering to the patient an anti-intellectual asthenia or anti-nervous asthenia therapeutically effective amount of a compound as defined in claim 3.

20. A method for the treatment of patients suffering from memory failures, comprising administering to the patient an anti-memory failure therapeutically effective amount of a compound as defined in claim 3.

21. A method for the treatment of patients suffering from senescence, comprising administering to the patient an anti-senescence therapeutically effective amount of a compound as defined in claim 3.

22. A method for the treatment of patients suffering from mental strain, comprising administering to the patient an anti-mental strain therapeutically effective amount of a compound as defined in claim 3.

* * * * *